US010829507B2

(12) United States Patent
Lohitharn (10) Patent No.: US 10,829,507 B2
(45) Date of Patent: Nov. 10, 2020

(54) DECOLORIZATION OF CONCENTRATED RHAMNOLIPID COMPOSITION (71) Applicant: Stepan Company, Northfield, IL (US)

(72) Inventor: Nattaporn Lohitharn, Chantilly, VA (US)

(73) Assignee: Stepan Company, Northfield, IL (US)

( * ) Notice: Subject to any disclaimer, the term of this patent is extended or adjusted under 35 U.S.C. 154(b) by 84 days.

(21) Appl. No.: 15/611,045

(22) Filed: Jun. 1, 2017

(65) Prior Publication Data
US 2018/0222934 A1 Aug. 9, 2018

Related U.S. Application Data (60) Provisional application No. 62/455,562, filed on Feb. 6, 2017.

(51) Int. Cl.
*C07H 1/06* (2006.01)
*C07H 15/04* (2006.01)
*B01F 17/00* (2006.01)

(52) U.S. Cl.
CPC .......... *C07H 1/06* (2013.01); *B01F 17/0021* (2013.01); *C07H 15/04* (2013.01)

(58) Field of Classification Search
CPC ............... C07H 1/06–08; C07H 15/00; C07H 15/02–06; C07H 15/10
See application file for complete search history.

(56) References Cited

U.S. PATENT DOCUMENTS

| | | | |
|---|---|---|---|
| 4,628,030 A | 12/1986 | Kaeppeli | |
| 4,814,272 A | 3/1989 | Wagner | |
| 4,902,512 A | 2/1990 | Ishigami | |
| 4,959,468 A * | 9/1990 | Ravi | C07H 15/04 127/46.1 |
| 5,013,654 A | 5/1991 | Banerjee | |
| 5,550,227 A | 8/1996 | Mixich | |
| 5,656,747 A | 8/1997 | Mixich | |
| 6,060,287 A | 5/2000 | Rocha | |
| 6,953,849 B2 | 10/2005 | Vali | |
| 7,202,063 B1 | 4/2007 | Gunther | |
| 9,005,928 B2 | 4/2015 | Schaffer | |

(Continued)

FOREIGN PATENT DOCUMENTS

| | | | |
|---|---|---|---|
| CA | 2164284 A1 * | 6/1996 | .......... B01F 17/0078 |
| CN | 1891831 A | 1/2007 | |

(Continued)

OTHER PUBLICATIONS

Petrovicova, E. Hydrogen peroxide in home-care formulations. INFORM Magazine. American Oil Chemists' Society. Nov. 2011. (Year: 2011).*

(Continued)

*Primary Examiner* — Stephen E Rieth
(74) *Attorney, Agent, or Firm* — Cheryl H. Agris; Agris & von Natzmer, LLP (57) ABSTRACT

Provided is a method for decolorizing and optionally neutralizing a rhamnolipid composition comprising treating said composition with a percarbonate salt as well as the decolorized and optionally neutralized composition obtainable therefrom. Also provided is a method for improving the quality of wastewater generated during said method.

4 Claims, 5 Drawing Sheets

(56) References Cited

U.S. PATENT DOCUMENTS

| | | |
|---|---|---|
| 9,884,883 B2 | 2/2018 | Lohitharn |
| 2011/0306569 A1 | 12/2011 | Yin |
| 2014/0296125 A1 | 2/2014 | Kuppert |
| 2014/0148588 A1 | 5/2014 | Schilling |
| 2014/0235561 A1 | 8/2014 | Blank |
| 2014/0296168 A1 | 10/2014 | Schilling |
| 2015/0011741 A1 | 1/2015 | Blank |
| 2015/0247151 A1 | 9/2015 | Schaffer |
| 2016/0272667 A1* | 9/2016 | Lohitharn .............. C07H 15/04 |
| 2016/0326561 A1 | 11/2016 | Lohitharn |

FOREIGN PATENT DOCUMENTS

| | | |
|---|---|---|
| CN | 1907916 A | 2/2007 |
| CN | 1908180 A | 2/2007 |
| CN | 1974589 | 6/2007 |
| CN | 101173210 | 5/2008 |
| CN | 101173238 | 5/2008 |
| CN | 101182560 A | 5/2008 |
| CN | 101265488 A | 9/2008 |
| CN | 101407831 A | 4/2009 |
| CN | 101538604 A | 9/2009 |
| CN | 101613725 A | 12/2009 |
| CN | 101705200 A | 5/2010 |
| CN | 101787057 A | 7/2010 |
| CN | 101845468 A | 9/2010 |
| CN | 101948786 A | 1/2011 |
| CN | 101948787 A | 1/2011 |
| CN | 102250790 A | 11/2011 |
| CN | 102432643 A | 5/2012 |
| CN | 102766172 A | 11/2012 |
| CN | 102796781 A | 11/2012 |
| CN | 102851059 A | 1/2013 |
| CN | 103146742 A | 6/2013 |
| CN | 103589765 A | 2/2014 |
| CN | 103966282 A | 8/2014 |
| CN | 104099388 A | 10/2014 |
| CN | 1115190 C | 1/2015 |
| CN | 104450825 A | 3/2015 |
| CN | 104498566 A | 4/2015 |
| CN | 104887539 A | 9/2015 |
| EP | 2410039 A1 | 1/2012 |
| JP | 1075796 | 3/1998 |
| JP | 2003052368 | 2/2003 |
| KR | 20060018783 A | 3/2006 |
| KR | 20070027151 | 3/2007 |
| KR | 100940231 | 2/2010 |
| KR | 1020130084760 | 7/2013 |
| WO | 2012010406 A1 | 1/2012 |
| WO | 2014039940 A1 | 3/2014 |
| WO | 2015030702 A2 | 3/2015 |
| WO | 2015085411 A1 | 6/2015 |
| WO | 2015091294 A1 | 6/2015 |

OTHER PUBLICATIONS https://www.alibaba.com/showroom/rhamnolipid.html, As viewed on Nov. 27, 2015.

Abdel-Mawgoud et al. (2009) "Characterization of Rhamnolipid Produced by Pseudomonas aeruginosa Isolate Bs20", Applied Biochemistry and Biotechnology 157:329-345.

Banat et al. (2010) "Microbial biosurfactants production, applications and future potential" Appl. Microbiol. Biotechnol. 37:427-444.

Deepika et al. (2015) "Characterization and antifungal properties of rhamnolipids produced by mangrove sediment bacterium Pseudomonas aeruginosa strain KVD-HM52", Biocatalysis and Agricultural Biotechnology 4:608-615.

Desai et al. (1997) "Microbial Production of Surfactants and Their Commercial Potential", Microbiol. Mol. Biol. Rev. 61: 47-64.

El-Fouly et al. (2015) "Biosynthesis of pyocyanin pigment by Pseudomonas aeruginosa", Journal of Radiation Research and Applied Sciences 8:36-48.

Essar et al. (1990) "Identification and characterization of genes for a second anthranilate synthase in Pseudomonas aeruginosa: interchangeability of the two anthranilate synthases and evolutionary implications", J Bacteriol. 172: 884-900.

Gautam et al. (2006) "Microbial surfactants: A review", J Oleo Sci 55:155-166.

Gong et al. (2015) "Rhamnolipid production, characterization and fermentation scale-up by Pseudomonas aeruginosa with plant oils", Biotechnology Letters 37:2033-2038.

Goswami et al. (2015) "Antifungal properties of rhamnolipid produced by Pseudomonas aeruginosa DS9 against Colletotrichum falcatum", Journal of Basic Microbiology 55:1265-1274.

Heyd et al. (2008) "Development and trends of biosurfactant analysis and purification using rhamnolipids as an axample", Anal. Bioanal. Chem. 391:1579-1590.

Jarvis et al. (1949) "A Glyco-lipide Produced by Pseudomonas Aeruginosa", J. Am. Chem. Soc. 71: 4124-4126.

Jayaseelan et al. (2014). "Pyocyanin: production, applications, challenges and new insights", World Journal of Microbiology and Biotechnology 30:1159-1168.

Lebrón-Paler (2008) "Solution and interfacial characterization of rhamnolipid biosurfactant from P. aeruginosa ATCC 9027", PhD Dissertation University of Arizona.

Long et al. (2012) "Two-step ultrafiltration of rhamnolipids using PSU-g-PEG membrane", J Membrane Sci. 409-410: 105-112.

Marchant et al. (2012) "Microbial biosurfactants: challenges and opportunities for future exploitation", Trends in Biotechnology 30:558-565.

Muller et al. (2012) "Rhamnolipids—Next generation surfactants?", J. Biotechnol. 162:366-80.

Mulligan et al. (1990) "Recovery of Biosurfactants by Ultrafiltration", J. Chem. Tech. Biotechnol. 47:23-29.

Nitschke et al. (2011). "Rhamnolipids and PHAs: Recent reports on Pseudomonas-derived molecules of increasing Industrial interest", Process Biochemistry 46:621-630.

Padilha et al. (2015) "Prediction of rhamnolipid breakthrough curves on activated carbon and Amberlite XAD-2 using Artificial Neural Network and Group Method Data Handling models", J. Mol. Liquids 206:293-299.

Rikalovic et al. (2013) "Comparative Analysis of Rhamnolipids from Novel Environmental Isolates of Pseudomonas aeroginosa", J. Surfact. Deterg. 16:673-682.

Rikalovic et al. (2012) "Production and characterization of rhamnolipids from Pseudomonas aeruginosa san-ai", Journal of the Serbian Chemical Society 77:27-42.

Sarachat et al., (2010) "Purification and concentration of a rhamnolipid biosurfactant produced by Pseudomonas aeruginosa SP4 using foam fractionation", Bioresource Technology 101:324-330.

Sekhon Randhawa et al. (2014) "Rhamnolipid biosurfactants—past, present, and future scenario of global market", Frontiers in Microbiology 5:1-7.

Smyth et al. (2010) "Isolation and Analysis of Low Molecular Weight Microbial Glycolipids", in Handbook of Hydrocarbon and Lipid Microbiology, K. N. Timmis (ed.), Springer-Verlag, Berlin, pp. 3705-3723.

Sodagari (2013) "Optimization of Production and Recovery of Rhamnolipids and Study of Their Effect on Bacterial Attachment", PhD Dissertation, University of Akron.

Wang et al. (2007) "Engineering bacteria for production of rhamnolipid as an agent for enhanced oil recovery", Biotechnology and Bioengineering 98:842-853.

Witek-Krowiak et al. (2011) "Ultrafiltrative separation of rhamnolipid from culture medium", World Journal of Microbiology and Biotechnology 27:1961-1964.

Zhang et al. (2016) "Separation and purification of six biosurfactant rhamnolipids by high-speed countercurrent chromatography utilizing novel solvent selection method", Separation Science and Technology, 51:673-680 (posted online Nov. 24, 2015).

Zhu et al. (2012) "Enhanced rhamnolipids production by Pseudomonas aeruginosa based on a pH stage-controlled fed-batch fermentation process", Bioresource Technology 117:208-213.

(56) References Cited

OTHER PUBLICATIONS

PCT/US2017/035403, International Search report and Written Opinion issued in connection with counterpart international application No., dated Nov. 6, 2017.
Related PCT appln. No. PCT/US2016/030721, International Search Report and Written Opinion dated Aug. 12, 2016.
Rhamnolipid Products. Agae Technologies (Feb. 28, 2017 from wayback machine); Retrieved from the internet on Jul. 8, 2018: url: http://www.agaetech.com/wp-content/uploads/2014/12/AGAE-Product-Samples3.png.

* cited by examiner

Figure 8

DECOLORIZATION OF CONCENTRATED RHAMNOLIPID COMPOSITION

FIELD

Provided is a method for decolorizing and optionally neutralizing a rhamnolipid composition comprising treating said composition with a percarbonate salt as well as the decolorized and optionally neutralized composition obtainable therefrom. Also provided is a method for improving the quality of the liquid phase generated (also referred to as the aqueous layer or wastewater) which contains a variety of organic and/or inorganic substances during from fermentation during said decolorization process.

BACKGROUND

The surface-acting agents or surfactants play an essential role in an industrial application especially personal cares and household cleaning products due to their ability to foam, clean, disperse, emulsify and lower surface tensions. Most surfactants available in the market are chemically derived from petroleum. Therefore, the demand of biosurfactants has been significantly increased due to their eco-friendly properties (i.e., biodegradability and biocompatibility) [1].

Rhamnolipids (RLs) are one of the most investigated and well known biosurfactants since they have high biodegradability, low toxicity, high foaming and the ability to be synthesized from renewable feedstock [2-4]. Rhamnolipids are interface-active glycolipids containing carbohydrates (rhamnose) and aliphatic acids (hydroxy fatty acids). RLs consist of one (monorhamnosylipids or mono-rhamnolipids) or two rhamnose units (dirhamnosylipids or di-rhamnolipids) and one or two (predominantly two) 3-hydroxy fatty acid residues. Several industrial applications include detergents and cleaners, antifungal [5, 6], cosmetics, bioremediation and enhanced oil recovery (EOR) [7].

The production of rhamnolipids includes an aerobic fermentation of bacteria predominately *Pseudomonas aeruginosa* with various carbon and nitrogen sources such as vegetable oil, crude glycerol, molasses, soap stock [8, 9]. The RL concentration is typically in the range of 1-50 g/L depending upon types of feedstock, fermentation condition and fermentation process [10-12]. Since the RL concentration obtained from the fermentation is very low, separation and purification are required afterwards to produce concentrated RL product (i.e., 30-90% RL concentration). The most common separation process starts with an acid precipitation. By adjusting the fermentation broth pH to 2-3 making the rhamnolipids insoluble in the aqueous solution and thus, precipitate out. A solvent extraction with ethyl acetate, hexane, chloroform-methanol and/orbutanol [13, 14] is also performed to further purify rhamnolipids from aqueous layer which is discarded. After stripping the solvent out [15], a concentrated viscous brownish-to-black oily rhamnolipid liquid is obtained.

However, only a small quantity of rhamnolipids is available on the market at high price. It is very hard to find the availability online without submitting a request order form. Among those listed for sale, the concentration of rhamnolipids with 90% or less contains dark brown color [16, 17]. The brownish-to-black color of concentrated rhamnolipids is possible due to the pigment, pyocyanin, produced by *P. aeruginosa* during fermentation [18-20]. The dark color of the concentrated rhamnolipids appears to be an issue when being used as a biosurfactant for personal care and household cleaning products. The current possible route to remove this color is to purify the concentrated rhamnolipids further using a thin layer chromatography (TLC) to remove color. However, the process is costly and time consuming which is unnecessary to do so for the personal cares and household cleaning application since the concentration of rhamnolipids used in these products is very low (less than 5%).

After separating rhamnolipids out, the aqueous layer is sent to a wastewater treatment plant since it contains a variety of inorganic and organic substances unconsumed during fermentation. The most commonly measured quality of wastewater is the biochemical oxygen demand (BOD). The higher the BOD, the higher organic maters in water thus, required more oxygen to break down those compounds which means a higher operating cost for the water treatment. The measurement for the total suspended solid (TSS) is also used to qualify the quality of the wastewater since they cause problem to aquatic life.

SUMMARY

Provided is an organic solvent-free process for obtaining a neutralized and decolorized composition comprising one or more rhamnolipids (RLs) comprising: (a) providing an aqueous medium comprising at least one rhamnolipid; (b) treating said medium provided with acid to obtain an acidic medium comprising a solid, liquid and oily phase; (c) removing at least the liquid phase from said acidic medium of (b) to obtain an acidic solid phase and optionally acidic oily phase and (d) treating said acidic solid phase and optionally acidic oily phase obtained in (c) with a composition comprising a percarbonate salt in an amount effective to neutralize and decolorize said acidic solid phase and optionally said acidic oil phase of step (c) to obtain said neutralized and decolorized composition. Also provided is a composition comprising a neutralized and decolorized solution obtainable therefrom. In a particular embodiment, the neutralization and decolorization step occurs at a temperature of between about 30-80° C. for at least about 30 minutes and in a more particular embodiment, to about 1 week. In a particular embodiment, the composition used in step (d) to decolorize and neutralize may further comprises a second base, e.g., NaOH. In a particular embodiment, percarbonate salt is present in a concentration of about 0.5-3% w/w equivalent hydrogen peroxide concentration (EHPC).

Also provided is a method for increasing the quality of the liquid phase obtained in step (b) comprising treating said liquid phase with an amount of percarbonate salt effective to increase said quality of the liquid phase. The quality of the liquid phase may be determined by measuring the biochemical oxygen demand (BOD) and/or total suspended solid (TSS). In a particular embodiment, provided is a method of reducing the BOD and/or TSS of at least about 25% in the liquid phase comprising treating said liquid phase with a composition comprising a percarbonate salt in an amount effective to reduce BOD and/or TSS of at least about 25% in said liquid phase. In a more particular embodiment, BOD and/or TSS is reduced at least about 30%, more particularly at least about 40%, even more particularly at least about 45%, yet even more particularly about 50%, yet even more particularly at least about 55% and even yet more particularly at least about 60%, wherein percarbonate salt is present at a concentration of about 0.2% to about 0.8% w/w EHPC.

DEFINITIONS

Where a range of values are provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this disclosure are incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

It must be noted that as used herein and in the appended claims, the singular forms "a," "and" and "the" include plural references unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. Thus the terms "comprising", "including," containing", "having" etc. shall be read expansively or open-ended and without limitation. When used herein, the term "comprising" can be substituted with the term "containing" or sometimes when used herein with the term "having".

DESCRIPTION OF SPECIFIC EMBODIMENTS

Provided is a process to reduce color of concentrated rhamnolipid solution (30-90%) using a sodium percarbonate ($Na_2CO_3 \times 1.5H_2O_2$). The starting material is an acidic rhamnolipid slurry (the solid rhamnolipid containing phases) obtained from the precipitation of rhamnolipid out of clarified broth at about pH 2.1 as described in U.S. application Ser. No. 14/992,995, filed Jan. 11, 2016 (published as US20160272667). The sodium percarbonate is added into the acidic rhamnolipid slurry at about 2-3% w/w equivalent hydrogen peroxide concentration (EHPC). Additional base such as NaOH can be used at about 0.5-1.5% w/w to bring the pH neutral if needed. Heating the solution at about 40-60° C. for 30 min. to several hours can speed up the decolorization process. After heating, the color of the concentrated rhamnolipids is lightened from black color like molasses to light brown or dark yellow color like honey. There is no loss of rhamnolipid concentration as a result of heating the solution.

Further provided as set forth in Example 3 is a process to increasing (alternatively referred to as enhancing) the quality of the liquid phase obtained. The increase in the quality of the liquid phase may be determined by BOD and/or TSS and/or OD measurements between about OD400 to about OD800.

Although US20160272667 discloses the decolorization of the rhamnolipids obtained from an organic solvent-free process with peroxide treatment using hydrogen peroxide ($H_2O_2$) or organic peroxide (peroxyacetic acid) or inorganic peroxide (sodium peroxide), the peroxides disclosed may have a high risk of flammability, health and reactivity based on the degree of hazard listed on NAFA 704 [21]. Unlike the abovementioned chemicals, sodium percarbonate is an eco-friendly chemical that has been used in the household word wide commercially named as "Oxyclean" [22]. The advantages of using a sodium percarbonate as a decoloring agent over the peroxides are:

1. Safer to transport since the sodium percarbonate is a soda ash with hydrogen peroxide combined in the stable white powder form;
2. The decolorization with sodium percarbonate takes place simultaneously with the neutralization step and thus, the process is shorter as compared to the decolorization step described in US20160272667;
3. The working volume is significantly reduced compared to US20160272667 since the starting material is the concentrated rhamnolipid solution not the aqueous medium (e.g., fermentation medium or broth) and thus, only a small volume being treated;

4. The process is significantly shorter. The process is done within 1 hour compared to 48 hours.

The process described here can be used in any fermentation product that is dark in color due to pigments produced by microorganisms.

EXAMPLES

Example 1: Color Removal of Acid-Form Concentrated Clarified Broth (ACCB) with Sodium Percarbonate Addition at 0.75-3% w/w Equivalent Hydrogen Peroxide Concentration (EHPC) at 60° C.

The starting material of this process is an acid-form concentrated clarified broth (ACCB) obtained from the precipitation of rhamnolipid out of clarified broth (CB) at pH 2.1 before neutralization step as described in US20160272667.

The pH of the starting material, ACCB, is around 2.1. Sodium percarbonate having a chemical formula of $Na_2CO_3 \cdot 1.5H_2O_2$ is added to ACCB at 0.75-3% w/w equivalent hydrogen peroxide concentration (EHPC). The samples are heated at 60° C. in baffle shake flasks with agitation at 250 rpm using MaxQ™ 8000 Stackable Orbital Shakers (Thermo Scientific) to ensure consistency of the agitation speed and temperatures of all samples.

Figure 1:
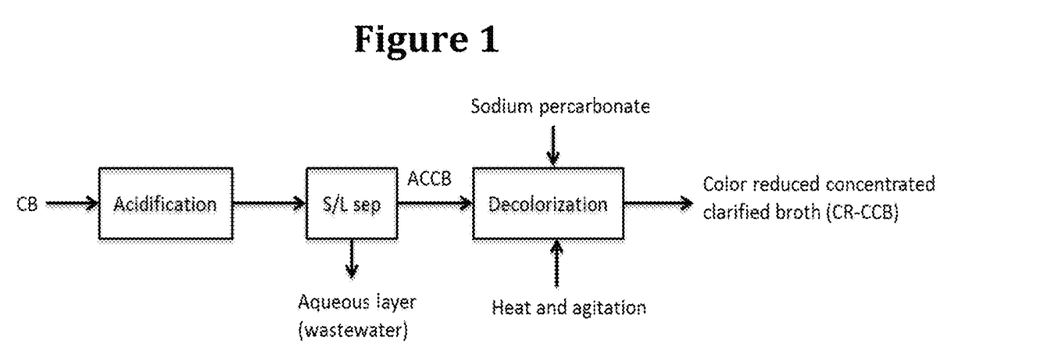
FIG. 1 schematically shows an overall process producing color reduced concentrated clarified broth (CR-CCB) with sodium percarbonate treated acid-form concentrated clarified broth (ACCB).
Figure 2:
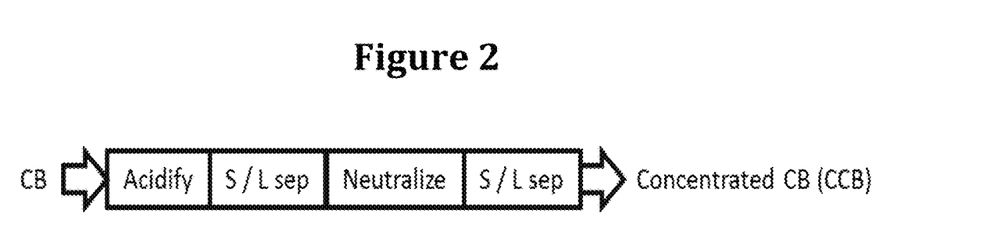
FIG. 2 schematically shows the reaction scheme used in Example 2 of U.S. application Ser. No. 14/992,995, filed Jan. 11, 2016 (published as US20160272667).
Figure 3:
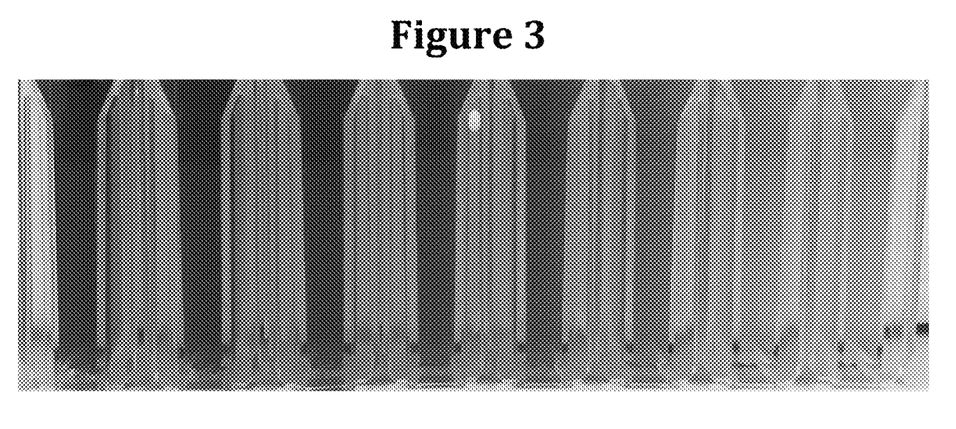
FIG. 3 shows a comparison of the color of the samples with sodium percarbonate addition at 0.75, 1, 1.25, 1.5, 2, 2.5 and 3% w/w EHPC (from left to right). Pictures were taken at 30 min of heating at 60° C. and 250 rpm.
Figure 4:
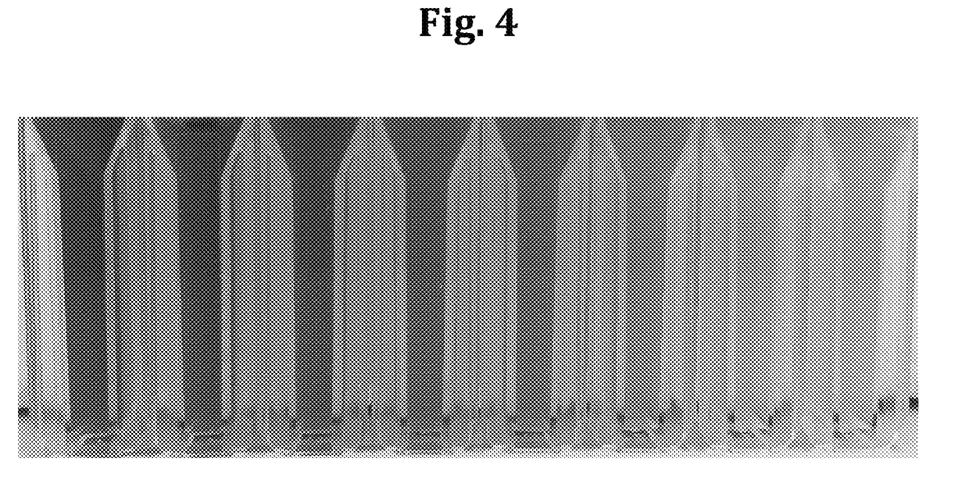
FIG. 4 shows a comparison of the color of the samples with sodium percarbonate addition at 0.75, 1, 1.25, 1.5, 2, 2.5 and 3% w/w EHPC (from left to right). Pictures were taken at 3 hours of heating at 60° C., 250 rpm.

A reduction in color of the samples with sodium percarbonate addition are shown in FIGS. 3 and 4.

Sodium hydroxide (NaOH) is added to the samples with sodium percarbonate addition less than 2% EHPC in order to bring the pH ~7. The amount of sodium percarbonate and NaOH added to the samples are shown in Table 1 along with the concentration of residue $H_2O_2$ in the samples after 4 hours of heating at 60° C.

TABLE 1

The amount of sodium percabonate, NaOH and hydrogen peroxide in the samples

| % EHPC | % Na percarbonate | % NaOH | pH | % $H_2O_2$ residue | % $H_2O_2$ consumption |
|---|---|---|---|---|---|
| 0.75% | 2.3% | 3.6% | 6.9 | 0.50% | 33% |
| 1.00% | 3.1% | 1.9% | 6.9 | 0.55% | 45% |
| 1.25% | 3.8% | 1.7% | 7.0 | 0.65% | 48% |
| 1.50% | 4.6% | 1.5% | 7.1 | 0.69% | 54% |
| 1.75% | 5.4% | 1.2% | 7.4 | 0.78% | 55% |
| 2.00% | 6.2% | 1.0% | 7.6 | 0.63% | 69% |
| 2.50% | 7.7% | 0% | 7.7 | 0.25% | 90% |
| 3.00% | 9.2% | 0% | 8.1 | 0.18% | 94% |

Figure 5:
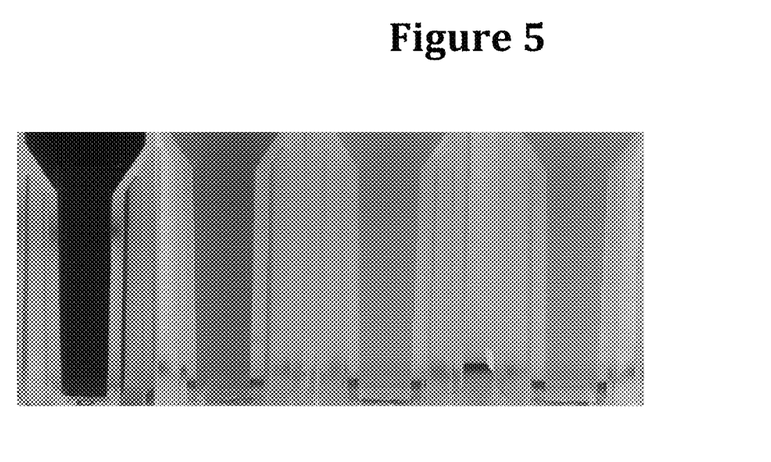
FIG. 5 shows the color of CCB obtained from Example 2 of US20160272667 (0% w/w EHPC, $1^{st}$ left) vs. the color of CR-CCB obtained from sodium percarbonate addition at 2, 2.5 and 3% EHPC after heating at 60° C., 250 rpm for 30 min (from $2^{nd}$ left to right).

The color of the concentrated clarified broth (CCB) is significantly reduced with the addition of sodium percarbonate from dark brown to very light yellow as seen in the FIG. 5.

Figure 6:
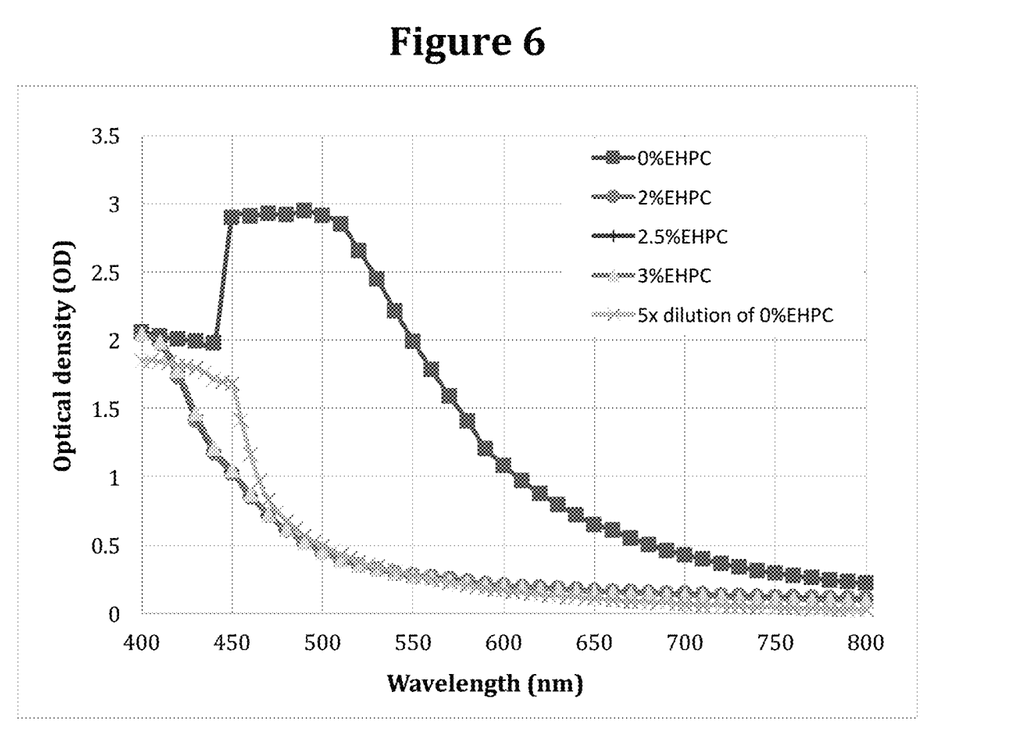
FIG. 6 shows the optical density of CCB sample (0% w/w EHPC) and CR-CCB with various sodium percarbonate concentrations (2-3% w/w EHPC) after heating at 60° C. for 3 hours.

The quantity of light absorbance or optical density (OD) of samples is measured at various wavelengths using a GENESYS™ 20 Visible Spectrophotometers (Thermo Scientific) in order to compare the concentration of light-absorbing constituent in the medium samples. Based on Beer's and Lambert's Laws, the higher the OD, the darker the sample. FIG. 6 clearly shows that the CCB sample designated as 0% EHPC (the $1^{st}$ left sample in FIG. 5) has the highest OD than the other samples with sodium percarbonate addition. By diluting the CCB sample (0% EHPC) 5 times with deionized water, the OD appears to be in the same range as those reduced color concentrated clarified broth (CR-CCB). This suggests that the color of the CR-CCB is relatively about the same darkest as 20% CCB. Please note that the starting material ACCB for this example is taken from the same batch/source and thus, the variation of the material is zero.

Example 2: Color Removal of Acid-Form Concentrated Clarified Broth (ACCB) with Sodium Percarbonate Addition at 1%-2.5% w/w Equivalent Hydrogen Peroxide Concentration (EHPC) at 45° C.

The starting material of this process is an acid-form concentrated clarified broth (ACCB) as described in Example 1. Sodium percarbonate is added to the starting material, ACCB, at 1%, 1.5%, 2% and 2.5% w/w equivalent hydrogen peroxide concentration (EHPC). Sodium hydroxide (NaOH) is also added to the samples with sodium percarbonate addition less than 2.5% w/w EHPC in order to bring the pH ~7.

Figure 7:
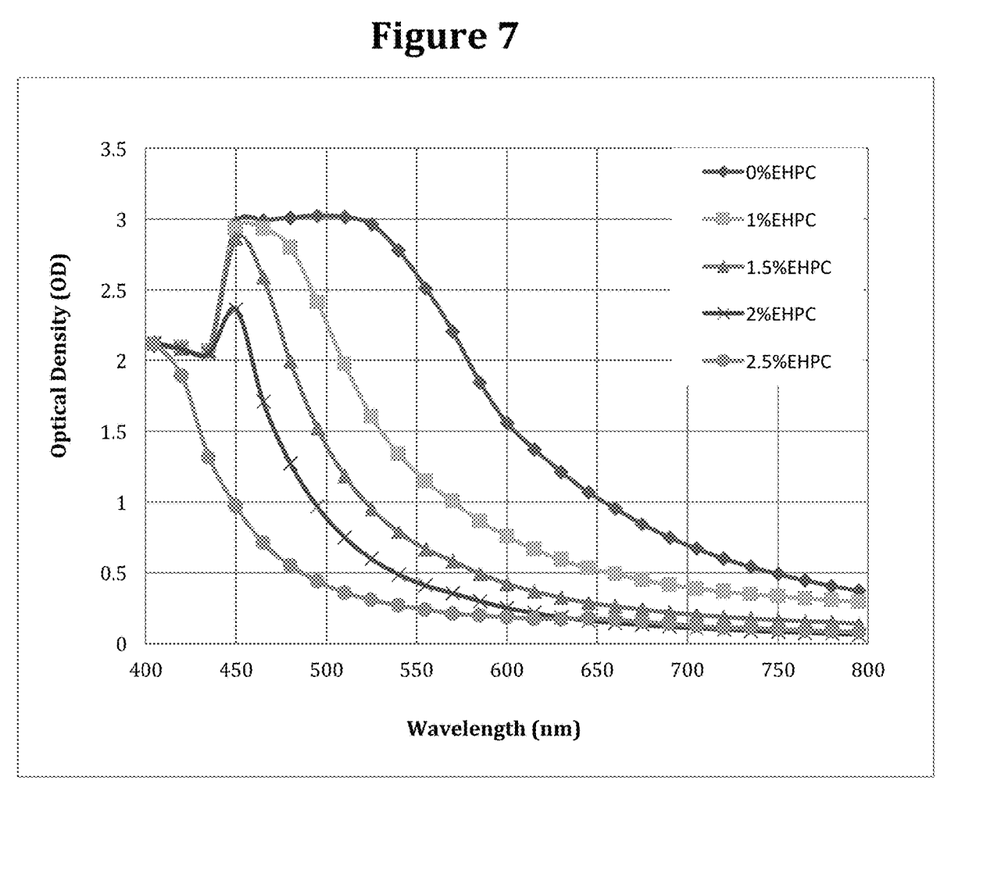
FIG. 7 shows the optical density of CCB sample (0% w/w EHPC) and CR-CCB with various sodium percarbonate concentrations (1-2.5% w/w EHPC) after heating at 45° C. for 4 hours.
Figure 8:
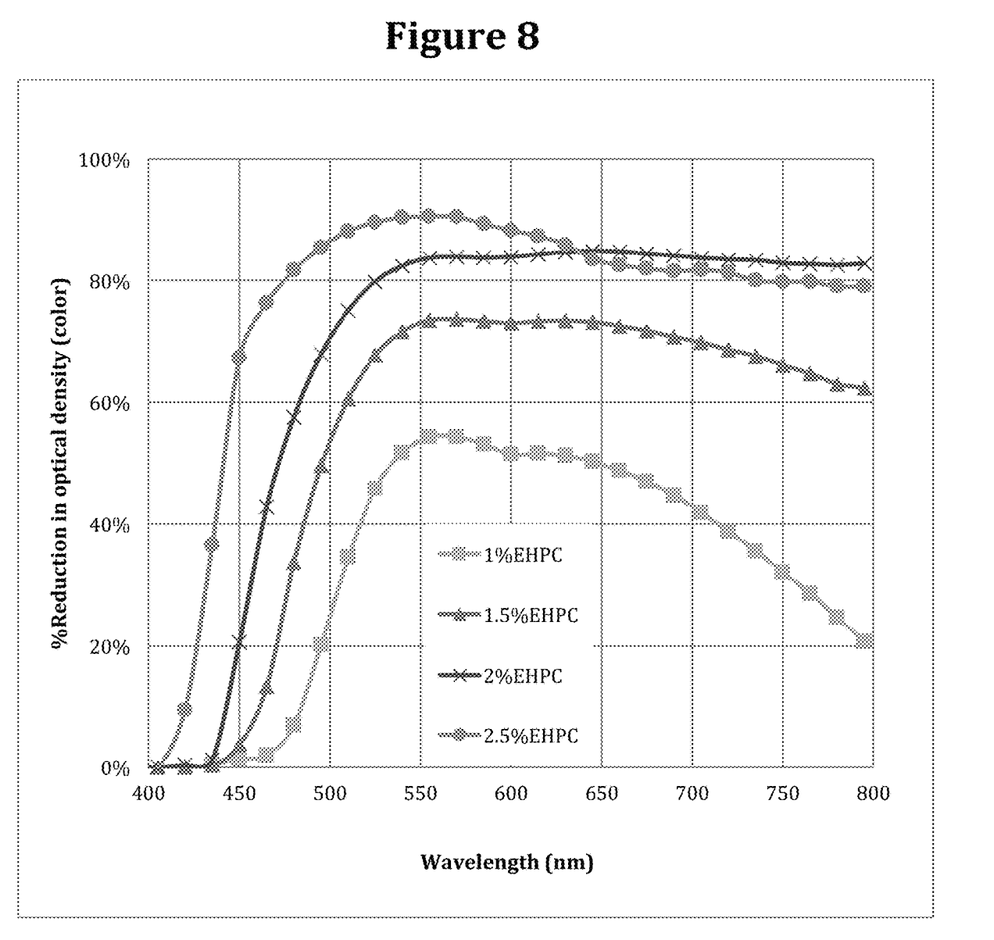
FIG. 8 shows the % reduction in optical density (color) of CR-CCB samples with 1-2.5% w/wEHPC compared to no sodium percarbonate addition (0% w/w EHPC) after heating at 45° C. for 4 hours.

The samples are then heated at 45° C. in non-baffle flasks with agitation at 350 rpm using MaxQ™ 8000 Stackable Orbital Shakers (Thermo Scientific) to ensure consistency of the agitation speed and temperatures of all samples. The degree of darkness of the samples is quantified with a GENESYS™ 20 Visible Spectrophotometers (Thermo Scientific) to measure the optical density (OD) of the samples at various wavelengths. The lower the OD value, the lighter the sample color. The optical density of the samples is shown in FIG. 7. The darkness color of the sample reduced with increasing the concentration of sodium percarbonate addition so as the OD value. The % reduction in optical density or color of the samples is also calculated against the sample without sodium percarbonate (0% w/w EHPC) and plotted in FIG. 8 which clearly supports this invention.

Example 3: Color Removal and Wastewater Quality Enhancement of the Aqueous Layer Waste Stream from Non-Organic Solvent Rhamnolipid Concentrated Process by Acid Precipitation Described in US20160272667 with Sodium Percarbonate Addition The aqueous (water) layer obtained from acid precipitation step of clarified broth (CB) to obtain concentrated rhamnolipid products described in Examples 2-6 of US20160272667 is considered a wastewater from this process which is a starting material for this example. Sodium percarbonate is added into this acidic wastewater stream at 0.25%, 0.5% and 0.75% w/w EHPC. After 1 hour of gentle agitation at 60° C., the samples are removed from heat and let to cool to room temperatures during 1-2 hours. Afterwards, the samples are subjected to optical density (OD) measurement and biological oxygen demand (BOD) and total suspended solid (TSS) analysis.

The optical density (OD) of the samples is measured with a GENESYS™ 20 Visible Spectrophotometers (Thermo Scientific). BOD and TSS are performed based on Standard Methods for the Examination of Water and Wastewater (available form www.standardmethods.org) 5210B and 2540, respectively). The % optical density at various wavelength (nm), % BOD and % TSS reductions of the samples are shown in Table 2. It clearly shows that treating the aqueous waste stream with sodium percarbonate at 0.5% w/w EHPC gives rise to the highest reduction of BOD and TSS while the most reduction in color is observed with 0.75% w/w EHPC sample at the studied wavelengths (400-

800 nm). The color of the aqueous layer is reduced with the addition of sodium percarbonate from brown to yellow.

TABLE 2

% Reduction of optical density at various wavelength, BOD and TSS of samples with sodium percarbonate addition. For example, OD 400 indicates optical density of samples at 400 nm.

| % EHPC | % Reduction | | | | | | |
|---|---|---|---|---|---|---|---|
| | OD 400 | OD 500 | OD 600 | OD 700 | OD 800 | BOD | TSS |
| 0.25% | 0% | 0% | 38% | 52% | 63% | 40% | 45% |
| 0.50% | 32% | 72% | 88% | 92% | 99% | 68% | 53% |
| 0.75% | 78% | 90% | 95% | 95% | 96% | 28% | −42% |

REFERENCES

1. Gautam, K. K. and V. K. Tyagi, *Microbial surfactants: A review*. J Oleo Sci, 2006. 55.
2. Sekhon, K. K. and P. K. S. M. Rahman, *Rhamnolipid biosurfactants—Past, Present and future scenario of global market*. Frontiers in Microbiology, 2014. 5: p. 1-7.
3. Müller, M. M., et al., *Rhamnolipids—Next generation surfactants?* Journal of Biotechnology, 2012. 162(4): p. 366-380.
4. Banat, I. M., et al., *Microbial biosurfactants production, applications and future potential*. Applied Microbiology and Biotechnology, 2010. 87(2): p. 427-44d.
5. Deepika, K. V., P. Ramu Sridhar, and P. V. Bramhachari, *Characterization and antifungal properties of rhamnolipids produced by mangrove sediment bacterium Pseudomonas aeruginosa strain KVD-HM52*. Biocatalysis and Agricultural Biotechnology, 2015. 4(4): p. 608-615.
6. Goswami, D., et al., *Antifungal properties of rhamnolipid produced by Pseudomonas aeruginosa DS9 against Colletotrichum falcatum*. Journal of Basic Microbiology, 2015. 55(11): p. 1265-1274.
7. Wang, Q., et al., *Engineering bacteria for production of rhamnolipid as an agent for enhanced oil recovery*. Biotechnology and Bioengineering, 2007. 98(4): p. 842-853.
8. Sodagari, M., *Optimization of Production and Recovery of Rhamnolipids and Study of Their Effect on Bacterial Attachment*, 2013, University of Akron.
9. Nitschke, M., S. G. V. A. O. Costa, and J. Contiero, *Rhamnolipids and PHAs: Recent reports on Pseudomonas-derived molecules of increasing industrial interest*. Process Biochemistry, 2011. 46(3): p. 621-630.
10. Gong, Z., Y. Peng, and Q. Wang, *Rhamnolipid production, characterization and fermentation scale-up by Pseudomonas aeruginosa with plant oils*. Biotechnology Letters, 2015. 37(10): p. 2033-2038.
11. Giani, C., et al. *Pseudomonas aeruginosa and its use in a process for the biotechnological preparation of L-rhamnose*. U.S. Pat. No. 5,501,966 A, Mar. 26, 1996, 1996.
12. Zhu, L., et al., *Enhanced rhamnolipids production by Pseudomonas aeruginosa based on a pH stage-controlled fed-batch fermentation process*. Bioresource Technology, 2012. 117: p. 208-213.
13. Heyd, M., et al., *Development and trends of biosurfactant analysis and purification using rhamnolipids as an example*. Analytical and Bioanalytical Chemistry, 2008. 391(5): p. 1579-1590.
14. Mixich, J., R. Rothert, and D. Wullbrandt Process for the quantitative purification of glycolipids. U.S. Pat. No. 5,656,747, Nov. 3, 1993, 1997.
15. Abdel-Mawgoud, A. M., M. M. Aboulwafa, and N. A.-H. Hassouna, *Characterization of Rhamnolipid Produced by Pseudomonas aeruginosa Isolate Bs20*. Applied Biochemistry and Biotechnology, 2009. 157(2): p. 329-345.
16. www.alibaba.com/showroom/rhamnolipid.hml. 2017 Jan. 17].
17. www.agaetech.com. 2017 [cited 2017 Jan. 17].
18. El-Fouly, M. Z., et al., *Biosynthesis of pyocyanin pigment by Pseudomonas aeruginosa*. Journal of Radiation Research and Applied Sciences, 2015. 8(1): p. 36-48.
19. Jayaseelan, S., D. Ramaswamy, and S. Dharmaraj, *Pyocyanin: production, applications, challenges and new insights*. World Journal of Microbiology and Biotechnology, 2014. 30(4): p. 1159-1168.
20. Essar, D. W., et al., *Identification and characterization of genes for a second anthranilate synthase in Pseudomonas aeruginosa: interchangeability of the two anthranilate synthases and evolutionary implications*. J Bacteriol, 1990. 172(2): p. 884-900.
21. en.wikipedia.org/wiki/NFPA_704
22. www.using-hydrogen-peroxide.com/sodium-percarbonate.html

What is claimed is:

1. An organic solvent-free process for obtaining a neutralized and decolorized composition comprising one or more rhamnolipids (RLs) comprising:
   (a) providing an aqueous medium comprising at least one rhamnolipid;
   (b) treating said medium provided with acid to obtain an acidic medium comprising a solid, liquid and oily phase;
   (c) removing at least the liquid phase from said acidic medium of (b) to obtain an acidic solid phase and optionally acidic oily phase;
   (d) treating said acidic solid phase and optionally acidic oily phase obtained in (c) with a composition comprising a percarbonate salt in an amount effective to neutralize and decolorize said acidic solid phase and optionally said acidic oil phase of step (c) to obtain said neutralized and decolorized composition, wherein said neutralization and decolorization occurs at a temperature of between about 45° C.-60° C. within about 0.5-4 hrs.

2. The method according to claim 1, wherein said composition comprising percarbonate salt used to treat said acidic solid phase and optionally acidic oily phase in (d) further comprises a second base.

3. The method according to claim 1, further comprising treating said liquid phase removed in step (c) with an amount of percarbonate salt.

4. The method according to claim 1, further comprising treating said liquid phase removed in step (c) with a composition comprising percarbonate salt in an amount effective to reduce biochemical oxygen demand and/or total suspended solid by at least about 25% in said liquid phase.

\* \* \* \* \*